United States Patent [19]

Illum

[11] Patent Number: 5,204,108
[45] Date of Patent: Apr. 20, 1993

[54] TRANSMUCOSAL FORMULATIONS OF LOW MOLECULAR WEIGHT PEPTIDE DRUGS

[75] Inventor: Lisbeth Illum, Nottingham, United Kingdom

[73] Assignee: Danbiosyst UK Ltd., Nottingham, United Kingdom

[21] Appl. No.: 469,443

[22] PCT Filed: Oct. 10, 1988

[86] PCT No.: PCT/GB88/00836

§ 371 Date: Apr. 9, 1990

§ 102(e) Date: Apr. 9, 1990

[30] Foreign Application Priority Data

Oct. 10, 1987 [GB] United Kingdom ................. 8723846

[51] Int. Cl.⁵ .......................... A61K 9/14; A61K 9/16; A61K 9/50; A61K 31/075
[52] U.S. Cl. ................................... 424/434; 424/435; 424/436; 424/489; 424/490; 424/491; 424/492; 424/494; 514/718
[58] Field of Search ................ 424/435, 436, 434, 489, 424/490, 491, 492, 494, 718

[56] References Cited

U.S. PATENT DOCUMENTS

| | | | |
|---|---|---|---|
| 4,250,163 | 2/1981 | Nagai et al. | 424/434 |
| 4,613,500 | 9/1986 | Suzuki et al. | 424/78 |
| 4,816,443 | 3/1989 | Brady et al. | 530/326 |

FOREIGN PATENT DOCUMENTS

| | | |
|---|---|---|
| 23359 | 11/1981 | European Pat. Off. . |
| 38979 | 11/1981 | European Pat. Off. . |
| 69399 | 3/1983 | European Pat. Off. . |
| 84898 | 8/1983 | European Pat. Off. . |
| 114577 | 8/1984 | European Pat. Off. . |
| 122036 | 10/1984 | European Pat. Off. . |
| 130577 | 5/1985 | European Pat. Off. . |
| 170642 | 10/1986 | European Pat. Off. . |
| 257915 | 3/1988 | European Pat. Off. . |
| 230264 | 12/1988 | European Pat. Off. . |
| 312052 | 4/1989 | European Pat. Off. . |
| 2081353 | 12/1971 | France . |
| 1516348 | 7/1978 | United Kingdom . |
| 2055578 | 3/1981 | United Kingdom . |
| 2176105 | 12/1986 | United Kingdom . |
| 88/0083 | 6/1987 | United Kingdom . |
| 8703197 | 6/1987 | World Int. Prop. O. . |
| 88/0456 | 6/1988 | World Int. Prop. O. . |

OTHER PUBLICATIONS

NATO ASI Series A: Life Sciences, vol., 1986, L. M. Sanders et al.: "Controlled delivery of Nafarelin, anantagonistic analougue of LHRH from microspheres of poly(D,L,lactic-co-Glycolic) acid", pp. 125-138.
Illum et al., *J. Pharm. Sci.*, 72(9), pp. 1086-1089 (1983).
L. Illum, NATO ASI Symp., "Microspheres as a Potential Controlled Release Nasal Drug Delivery System", 205-210 (1986).
Illum et al., *Int. J. Pharm.*, 39, 189-199 (1987).
Salzman et al., *New Engl. J. Med.*, 312, pp. 1078-1084 (1985).
Hanson et al., *Advanced Delivery Systems for Peptides & Proteins*, 233-242 (1988).
L. Illum, *Archiv for Pharmaci og Chemi*, 94, 127 (1987).
*J. Controlled Release*, 1, 15-22 (1984).
Abstract of Teijin Japanese Appln. No. 61/194034.
*J. Pharm. Pharmacol.*, Morimoto et al., 37, 134-36 (1985).

*Primary Examiner*—Thurman K. Page
*Assistant Examiner*—Carlos Azpuru
*Attorney, Agent, or Firm*—Lorusso & Loud

[57] ABSTRACT

A drug delivery composition comprising a plurality of microspheres and active drug associated with each microsphere, the drug being for systemic delivery and having a maximum molecular weight of 6000, and the composition being substantially free of an enhancer. The microspheres may be of starch, gelatin or albumin. Suitable drugs include peptides, such as insulin, and antigenic vaccine ingredients. The compositions are suitable for delivery across a mucosal surface such as the vagina, eye or nose.

13 Claims, 8 Drawing Sheets

TRANSMUCOSAL FORMULATIONS OF LOW MOLECULAR WEIGHT PEPTIDE DRUGS

The present invention relates to drug delivery compositions and more particularly to a composition which provides for the uptake of active drug material across mucosal surfaces, such as the vagina or the nasal cavity.

A major problem in drug delivery is the effective absorption of high molecular weight material such as proteins and peptides across biological membranes. Normally such molecules are not taken up by the body if administered to the gastrointestinal tract, to the buccal mucosa, to the rectal mucosa, the vaginal mucosa or given as an intranasal system. Recent studies with the material insulin have demonstrated that the absorption of such a compound can be increased if it is given together with a so-called absorption enhancer. These absorption enhancing materials have included surfactants of the non-ionic type as well as various bile salt derivatives. An increased permeability of membranes in the presence of these types of surfactant material is not unexpected, indeed the literature in the field of gastroenterology contains a wide range of such absorption promoters. (For a review see Davis et al. (editors), Delivery Systems for Peptide Drugs, Plenum Press, New York, 1987). However, such materials will probably not be acceptable for the chronic administration of pharmacological agents because of their irritant effects on membranes. This includes not only the non-ionic variety of surface active agents but also bile salts and bile salt derivatives (e.g. fusidic acid).

EP-A-023,359 and EP-A-122,023 describe a powdery pharmaceutical composition for application to the nasal mucosa and methods for administration thereof. The pharmaceutical composition allows polypeptides and derivatives thereof to be effectively absorbed through the nasal mucosa. Similarly, U.S. Pat. No. 4,250,163 describes a method for administering a medicament to the nasal mucosa where the preferred composition has mucoadhesive properties.

EP-A-230,264 describes an aqueous nasal drug delivery system for vaccines containing a high molecular weight drug, a gelling agent (e.g. hydroxyethylcellulose) and in some cases other additives (e.g. surfactants, glycerol and polyethyleneglycol).

None of the above patents and applications describes the use of microspheres for nasal administration.

A microsphere preparation for nasal delivery has been described in PCT/GB86/00721 (Fisons). This refers only to one specific drug (sodium cromoglycate) for local effect rather than delivery to the general circulation. (See also J. Controlled Release, 1, 15-22, 1984). Most importantly, the function of the ion exchange materials was to keep the drug in contact with the mucosal surface for longer periods not to enhance absorption.

Similarly, Morimoto and colleages (J. Pharm. Pharmacol. vol 37 pages 135-136 1985) have used a nasal gel (once again polyacrylic acid) as delivery system for insulin and calcitonin in rats. A significant decrease in plasma glucose levels was obtained as compared to the normal formulation, indicating an increase in the absorption efficiency.

At the present time the nose is being proposed as an alternative route for the delivery of drugs that will act within the systemic circulation. Particular attention is being focused on nature-identical peptides or proteins, or analogues or fragments thereof, produced by recombinant DNA techniques. Other drugs that are being are extensively metabolised either in the gastrointestinal tract itself or are subject to first pass metabolism in the liver.

However, most polypeptide drugs show a low bioavailability when administered intranasally.

The rapid clearance of nasal sprays from the nose can probably be considered to be a major factor in influencing loss of drugs from potential absorption surfaces. In addition, in the case of peptides and proteins, enzymatic degradation of the drug and molecular size may also have a role in giving low bioavailabilities.

Our earlier co-pending application PCT/GB 88/00396 discloses intra-nasal microsphere formulations containing an enhancer. We have now found that, with peptide drugs of molecular weight below 6000, an enhancer is not required and, in fact, is undesirable.

One aspect of the present invention therefore provides a transmucosal drug delivery composition comprising a plurality of microspheres and active peptide associated with each microsphere, the drug being for systemic delivery and having a maximum molecular weight of 6000 (preferably at least 1000), and the composition being substantially free of an enhancer.

By "enhancer", we mean any material which acts to increase absorption across the mucosa. Such materials include mucolytic agents, degradative enzyme inhibitors and compounds which increase permeability of the mucosal cell membranes. Specifically, all the enhancers disclosed in PCT/GB 88/00396 are excluded from the present compositions. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree.

The term "drug" is used to embrace any pharmacologically active peptide, including small molecules, hormones, polypeptides and vaccines or components thereof, for example isolated antigens or antigenic parts or mimics thereof.

Preferably the microspheres are administered in the form of a freeze-dried powder by spraying and have bioadhesive properties. The microspheres should be of a size between 10 and 100 microns, preferably 40-60 μm, (after swelling) and prepared from a biocompatible material that will gel in contact with the mucosal surface. Substantially uniform, solid microspheres are preferred. Starch microspheres (cross linked if necessary) are a preferred material. Other microspheres include gelatin, albumin, collagen, dextran and dextran derivatives. Preparation of these microsphere systems is well described in the pharmaceutical literature (see for example Davis et al., (Eds), "Microspheres and Drug Therapy", Elsevier Biomedical Press, 1984). Emulsion and phase separation methods are both suitable. The final microspheres can be modified by chemical crosslinking or heat treatment. The active agent can be incorporated into the microspheres during their formulation or sorbed into/onto the system controlled by the physical nature of the microsphere matrix and, for example, the extent of the crosslinking. The microsphere delivery systems may also include microspheres made from the active peptide or protein itself such as insulin microspheres.

As an added advantage the particles may have variable controlled release characteristics through modifications made to the microsphere system, for example by controlling the degree of cross-linking or by the incorporation of excipients that alter the diffusional properties of the administered drug. The amount of drug that can be carried by the microspheres is termed the loading capacity, which is determined by the physicochemical properties of the drug molecule and in particular its size and affinity for the particle matrix. Higher loading capacities are to be expected when the administered drug is incorporated into the microspheres during the actual process of microsphere manufacture. It is known that for many peptides and proteins the amount of drug substance to be administered for a resultant therapeutic effect will be of the order of a few milligrams or less. Microcapsules of a similar size, which are bioadhesive and which have controlled release properties, would also be expected to provide similar benefit in terms of an increased and modified bioavailability of administered drugs. These microcapsules can be produced by a variety of methods. The surface of the capsule could be adhesive in its own right or could be modified by coating methods familiar to those skilled in the art. These coating materials are preferably bioadhesive polymers such as polycarbophil, carbopol, DEAE-dextran or alginates. These microcapsules are deemed to be "microspheres" for the purposes of this specification and again, are preferably 10–100 μm in diameter.

Using the combination of microspheres and drug, it has been found that the bioadhesive microsphere systems have the ability to enhance greatly the bioavailability of polar drugs when they are administered together.

This potentiation of effect is believed to be due to the greater retention of the delivery systems in the nasal cavity.

The microsphere composition can also afford protection of the drug against degradation by enzymes.

The compositions may be used with drugs selected from the following non-exclusive list: insulin, calcitonins (for example porcine, human, salmon, chicken or eel) and synthetic modifications thereof*, enkephalins*, LHRH and analogues* (Nafarelin, Buserelin, Zolidex), GHRH (growth hormone releasing hormone)*, nifedipin, THF(thymic humoral factor)*, CGRP (calcitonin gene related peptide)*, atrial natriuretic peptide*, antibiotics, metoclopramide*, ergotamine*, Pizotizin*, nasal vaccines (particularly AIDS vaccines, measles, rhinovirus Type 13 and respiratory syncitial virus)* and pentamidine.

The starred drugs are especially preferred for administration with the microsphere system of the invention.

Administration

The microspheres can be administered via the nasal route using a nasal insufflator device or pressurized aerosol cannister. Example of these are already employed for commercial powder systems intended for nasal application.

Thus, a further aspect of the invention provides a method of treating a human or other mammal by administering a formulation as described above to a mucosal surface of that human or other mammal, for example the vagina, eye or nose.

Embodiments of the present invention will now be described by way of example and with reference to the accompanying drawings.

Figure 1:
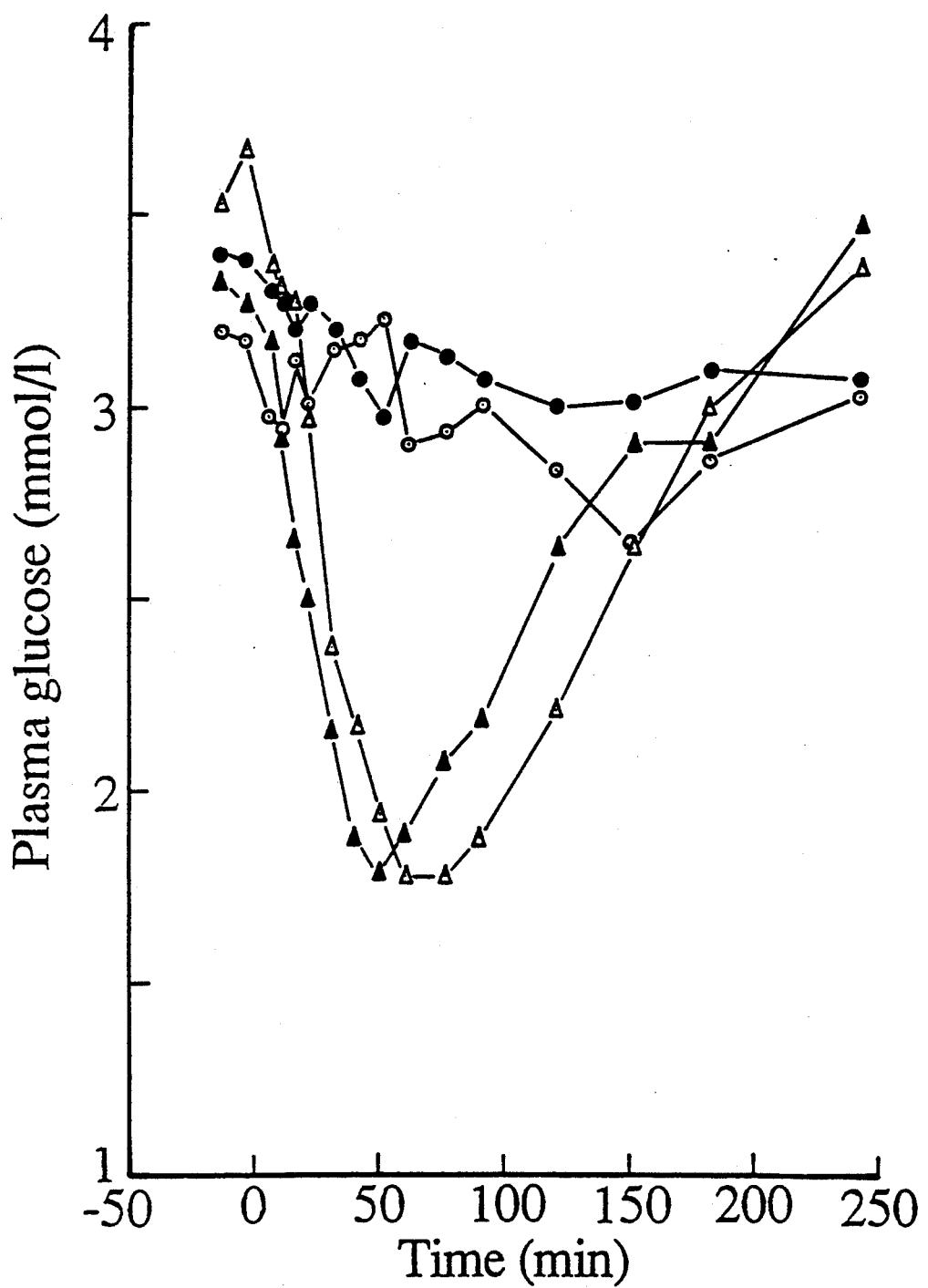
FIG. 1 shows plasma glucose levels in sheep obtained for administration intranasally of insulin in different delivery forms and intravenously.

The microspheres are readily available, for example starch ones are available as "Spherex" (Pharmacia), but may in general be made by the methods given in Davis et al., loc. cit. The following are specific Examples.

ALBUMIN MICROSPHERES 10 ml of a 25% HSA solution (pH=5) was stirred (500 rpm) while a 30% solution of PEG was added (about 2.5 ml) until phase separation occurred. The system was stirred for 15 min before the albumin droplets were solidified by slowly heating the mixture to 90° C. and keeping it at this temperature for 30 min. Instead of heat denaturation, glutaraldehyde can be used to crosslink the albumin but this latter method seems to make the particles aggregate to a greater extent than that seen with the heat denaturation. The microspheres were then isolated by filtration and freeze dried.

With a stirring speed of 500 rpm, particles with a means size of 43 μm±6 μm were produced.

STARCH MICROSPHERES 15 ml of 5% starch solution (pH=7) was kept at a constant temperature of 70° C. and stirred (500 rpm) while a 30% solution of PEG was added (about 7 ml) until phase separation had occurred. The system was then stirred for a further 15 min, before it was cooled on ice during constant stirring. The microspheres were then isolated by filtration and freeze dried. With a stirring speed of 500 rpm, particles with a mean size of 33 μm±10 μm were produced.

GELATINE MICROSPHERES 30 ml of 10% bovine gelatine (pH=8.5) was kept at a constant temperature of 50° C. and stirred (500 rpm) while a 30% solution of PEG was added (about 20 ml) until the coacervation region was reached. To control this step, a nephelometer can be used. The mixture was cooled on ice during constant stirring. The microspheres were isolated by filtration and freeze dried.

With a stirring speed of 500 rpm, particles with a mean size of 60 μm±10 μm were produced.

GELATINE MICROSPHERES CONTAINING INSULIN 10 ml of 2.5% Zn-insulin was precipitated with a little 0.1 N HCl while stirring and was then mixed with 10 ml 10% Porcine Gelatine, the temperature being kept constant at 35° C.. While stirring this mixture, a 30% solution of PEG was added (about 8 ml) until coacervation had occurred. The system was then cooled on ice and the microspheres isolated by filtration and freeze dried.

ALBUMIN MICROSPHERES CONTAINING INSULIN

These microspheres were prepared by the coacervation method.

To 5 ml 20% (w/v) Human Serum Albumin (pH=5), stirred at 500 rpm, was slowly added 5 ml of 2.5% Zn-insulin (pH=6.7), and the low pH of the albumin solution precipitated the insulin. To this was added a 30% solution of PEG 4000 (about 2 ml) until the formation of particles. Then 100 µl of 25% glutaraldehyde was added and the mixture was stirred for 3 min before 15 ml of distilled water was added to prevent aggregation of the albumin particles. The cross-linking was allowed to continue for a total of 20 min. The particles were isolated by filtration, washed with distilled water (pH=5) and freeze dried.

The preparation of a starch-insulin system was carried out by adding the freeze-dried starch microspheres to a phosphate buffer solution (pH=7.3) containing the insulin, mixing for 1 hour and freeze-drying until a light powder was obtained. A typical concentration of insulin would be 1 IU/mg microspheres. The microspheres can be loaded with less or more drug.

Nasal delivery studies

The following studies of nasal delivery in an animal model (sheep) and in man have been carried out.

Insulin

In all animals studied the glucose plasma levels were analysed using the glucose oxidase method. The plasma insulin levels were determined for the sheep experiments by means of a radioimmune assay using a double-antibody technique.

EXAMPLE 1: Sheep Studies

Zn-crystallized highly purified semisynthetic human insulin was used, each 1 mg of pure protein being equivalent to 28 IU insulin. Insulin solutions were prepared in 1/75M phosphate buffer (pH 7.3).

Eighteen cross-bred (Suffolk and Texel) sheep were used in this study. For intranasal administration of solutions, a blueline umbilical cannula of 35 cm length (size 6 FG) was inserted into the nostril of the sheep to a preset depth of 10 cm before the delivery of the solution from a 1 ml syringe. For intranasal administration of powdered formulations, a BOC endotracheal tube (red rubber, cuffed) of 6.5 mm was loaded with the powder formulation and then inserted into the nostril of the sheep to a preset depth of 6 cm before blowing the powder into the nasal cavity.

The mean weight in kg of the sheep (±S.D.) was 35.9 (±2.7). The animals were not fasted prior to insulin administration because it is difficult to achieve this in practice and because of the possibility of inducing insulin resistance in the animals. The latter term means that under such conditions the sheep blood glucose levels would not respond as readily to the insulin administered.

Preparation of insulin solutions and powders:

Insulin stock solutions were prepared in 1/75 M phosphate buffer (pH 7.3). These were then used as liquid formulations for intravenous and intranasal administrations, and also in the preparation of the lyophilised microsphere formulations. The latter were prepared by dispersing the required quantity of microspheres in the insulin solution, stirring for 1 hour at room temperature, and then freeze-drying to obtain the powder formulation.

Administration of insulin formulations:

Insulin was administered at 0.1 IU/kg via the intravenous route, at 0.2 IU/kg via the subcutaneous route, and at 2 IU/kg via the nasal route. Three sheep were used in each experiment.

(1) Intravenous administration of insulin as an aqueous solution prepared at 4 IU/ml.
(2) Intranasal administration of an aqueous solution, prepared at 200 IU/ml.
(3) Intranasal administration of insulin in combination with starch microspheres (2.5 mg/kg) as a lyophilised powder. To prepare the formulation, 500mg of Spherex were dispersed in 30 ml of 1/75 M phosphate buffer (pH 7.3) containing 400 IU insulin, mixed for 1 h, and then freeze-dried.
(4) Intranasal administration of insulin in combination with starch microspheres (2.5 mg/kg). The sheep were dosed twice, with 4 hours between the doses. The preparation of the formulation was as in (3) above.
(5) Intranasal administration of starch microspheres (2.5 mg/kg) without insulin (control). To prepare the formulation, 500 mg of Spherex were dispersed in 30 ml of 1/75 M phosphate buffer (pH 7.3), mixed for 1 h, and then freeze-dried.
(6) Subcutaneous administration of insulin as an aqueous solution prepared at 4.2 IU/ml.

Blood samples of 5 ml were collected onto crushed ice from the cannulated jugular vein of the sheep. Each blood sample was divided into two parts. For insulin analysis, the blood collected (2.5 ml) was mixed gently in 5 ml heparinised (Li Heparin) tubes. For glucose analysis, the blood collected (2.5 ml) was mixed gently in 5 ml fluoride oxalate tubes. All blood samples following withdrawal were maintained on crushed ice, awaiting centrifugation which was then performed at 4° C. and 3000 rpm. The plasma collected was stored at −20° C. awaiting insulin and glucose analysis (radioimmuno assay for insulin).

Figure 2:
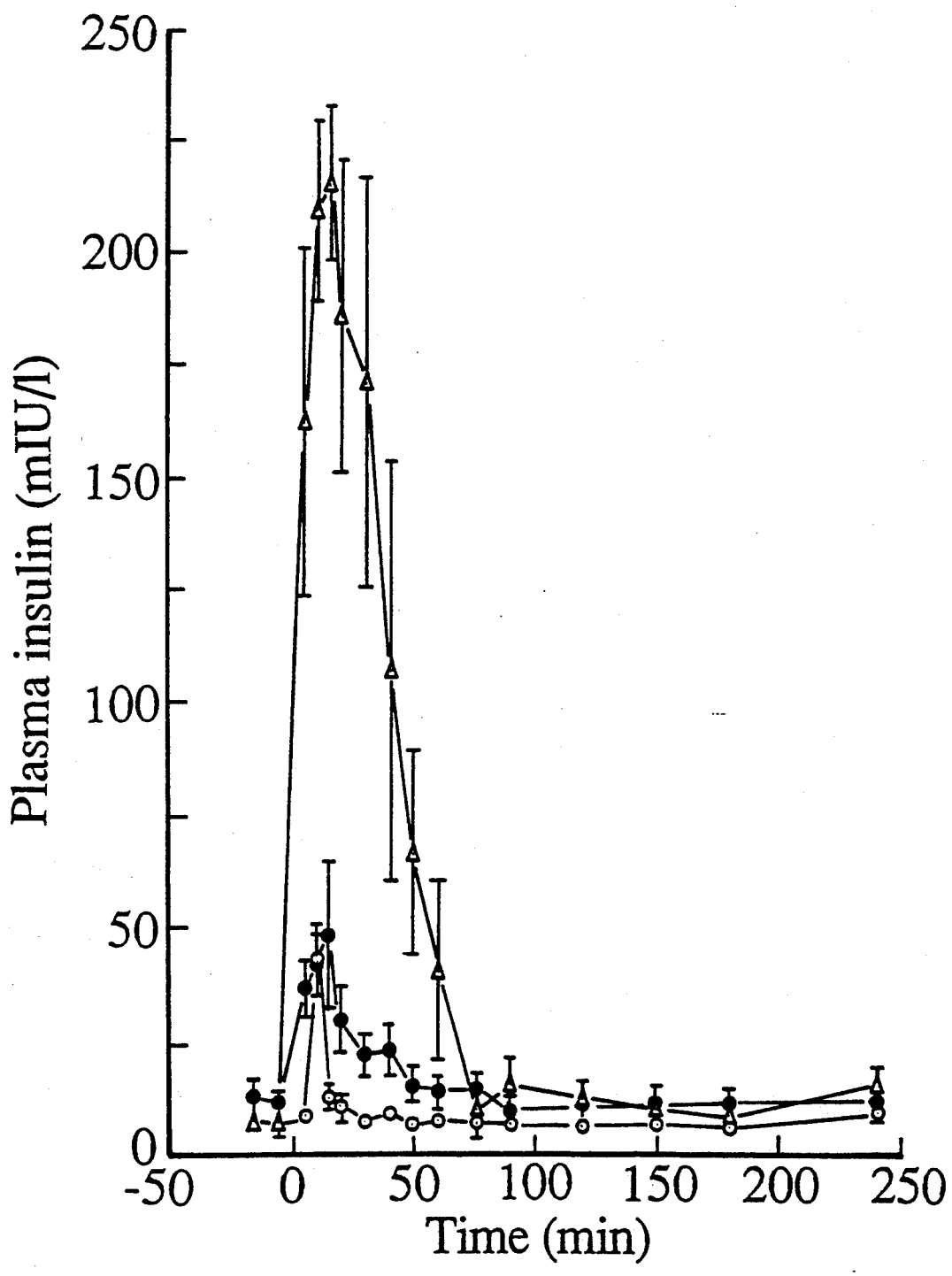
FIG. 2 shows the corresponding curves for plasma insulin levels in sheep.

FIG. 1 shows the plasma glucose levels obtained for intranasal administration of a simple insulin solution, of blank starch microspheres, of insulin in the combined microsphere formulation and the intravenous administration of insulin. FIG. 2 shows the corresponding curves for plasma insulin levels. It can be seen that insulin administered intra-nasally as a simple solution does not have a significant effect on the plasma glucose level and the amount of insulin being absorbed via this route is indeed very low. The legends to FIGS. 1 and 2 can be found on page 21.

The administration of the insulin in combination with the starch microspheres results in an 180% increase in AUC of plasma insulin as compared to a simple nasal insulin solution. At the same time the peak insulin level is increased by 350%. The sharp level peak appears at 15-20 min and decreases rapidly as for intravenous insulin.

Figure 3:
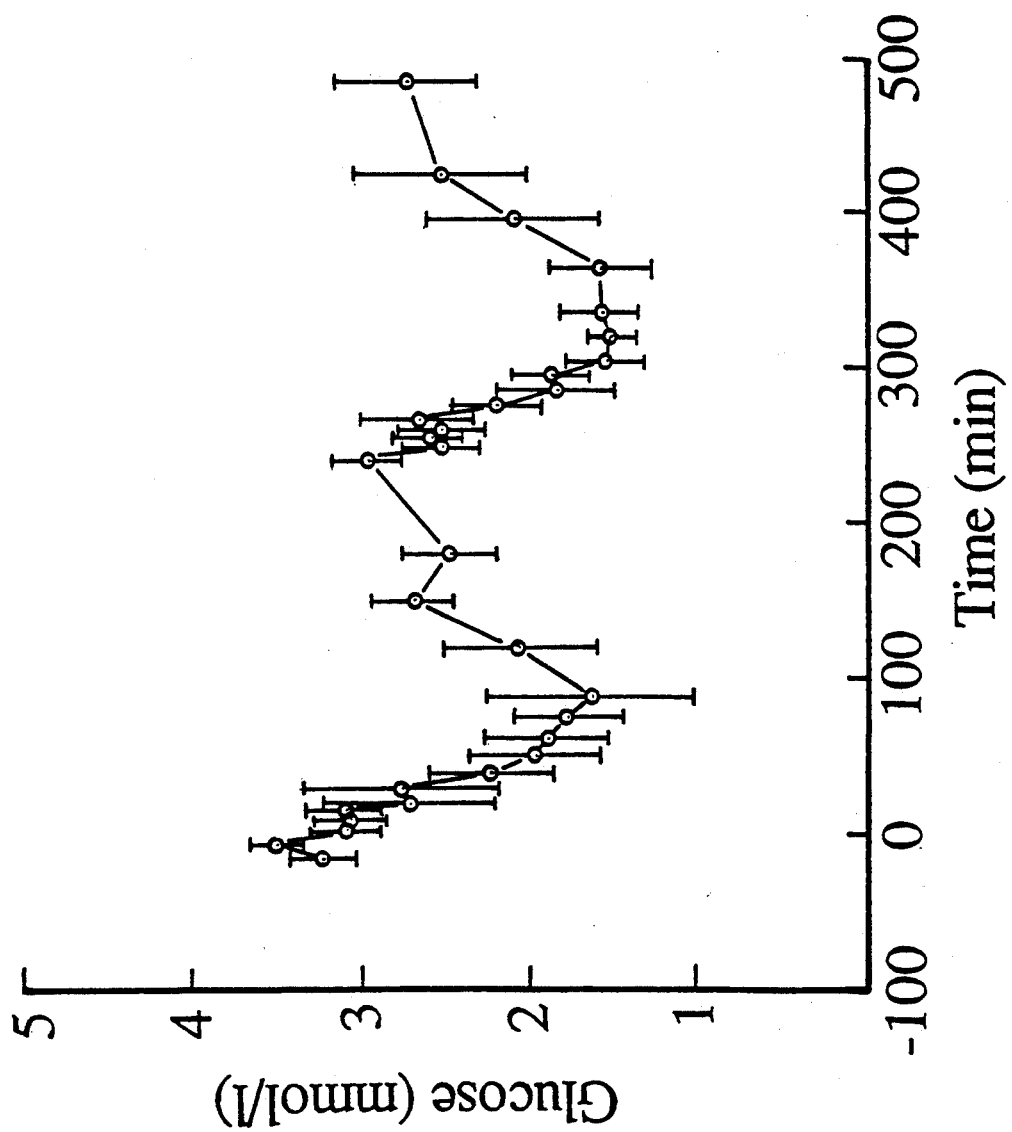
FIG. 3 shows plasma glucose levels in sheep for repeated dosing of insulin in combination with starch microspheres.
Figure 4:
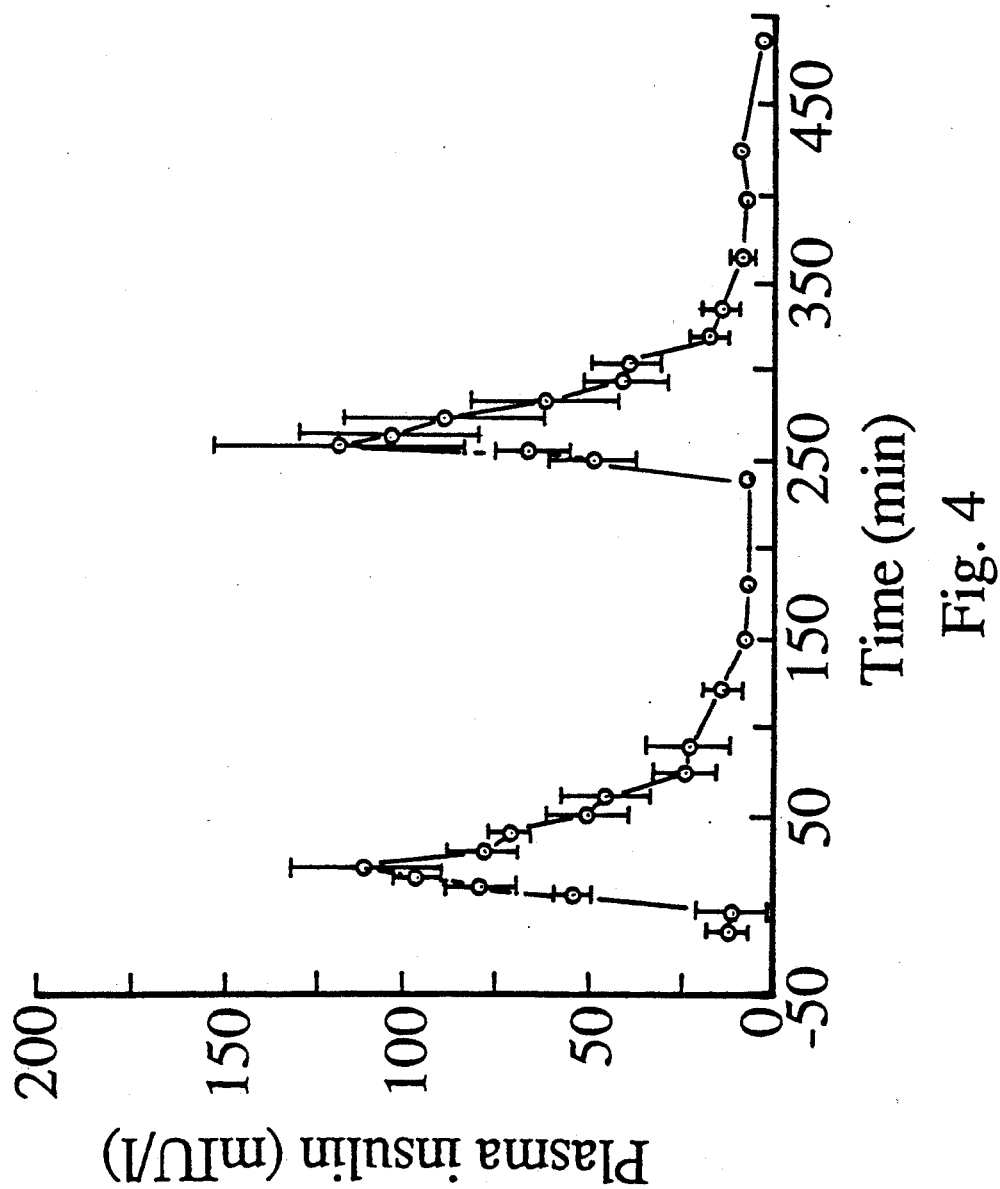
FIG. 4 shows due corresponding curves for plasma insulin in sheep.

FIG. 3 shows the plasma glucose levels after the double dosing of insulin in combination with starch microspheres. A constant dose response effect is obtained, with the lowest peak glucose level about 50 min after the first dosing and 55 min after the second dosing. There seems to be no interference between the response from the second application and the first. For the plasma insulin levels (FIG. 4) a similar picture was obtained with two separate nice sharp peaks appearing after 15 min and 35 min after the first and second dosing, respectively.

EXAMPLE 2: Human studies—insulin

Healthy, non smoking, male and female volunteers (weight range 50-70 kg) were recruited for this study. The two formulations a) insulin (1 IU/kg) in combination with starch microspheres (1 mg/kg) and b) microspheres alone (1 mg/kg), were administered after an overnight fast. The formulations were administered using a nasal insufflator system. Blood glucose levels were monitored every 5 min obtaining blood samples from an indwelling cannula inserted retrogradely into the dorsal hand vein.

Na-crystallized highly purified semisynthetic human insulin was used, each 1 mg of pure protein being equivalent to 28 IU insulin. The insulin microsphere formulation was prepared as for the sheep studies; however, the insulin solution was prepared without the use of phosphate buffer.

Figure 5:
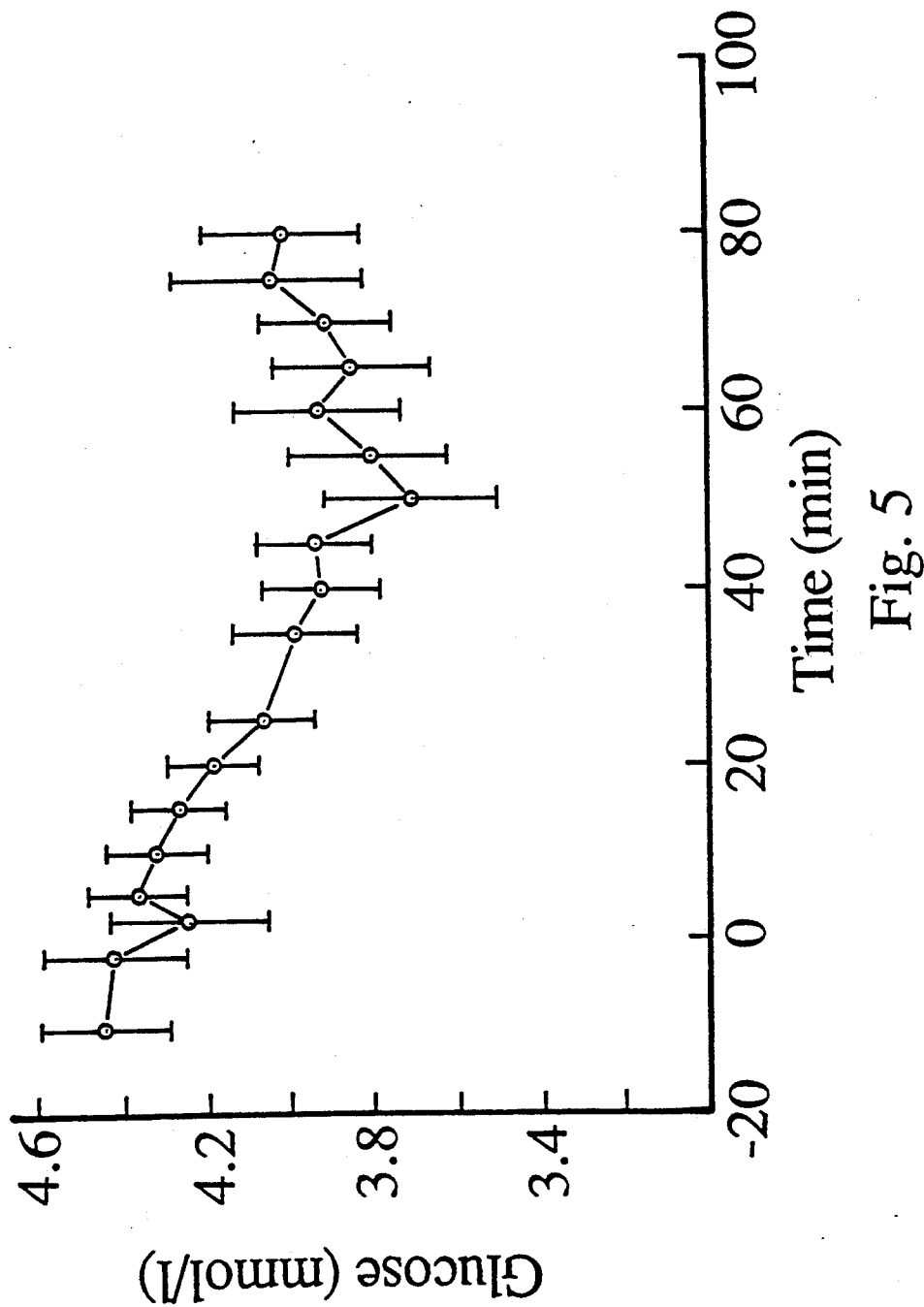
FIG. 5 shows plasma glucose levels in man (n=5) obtained for administration intranasally of insulin in combination with starch microspheres.
Figure 6:
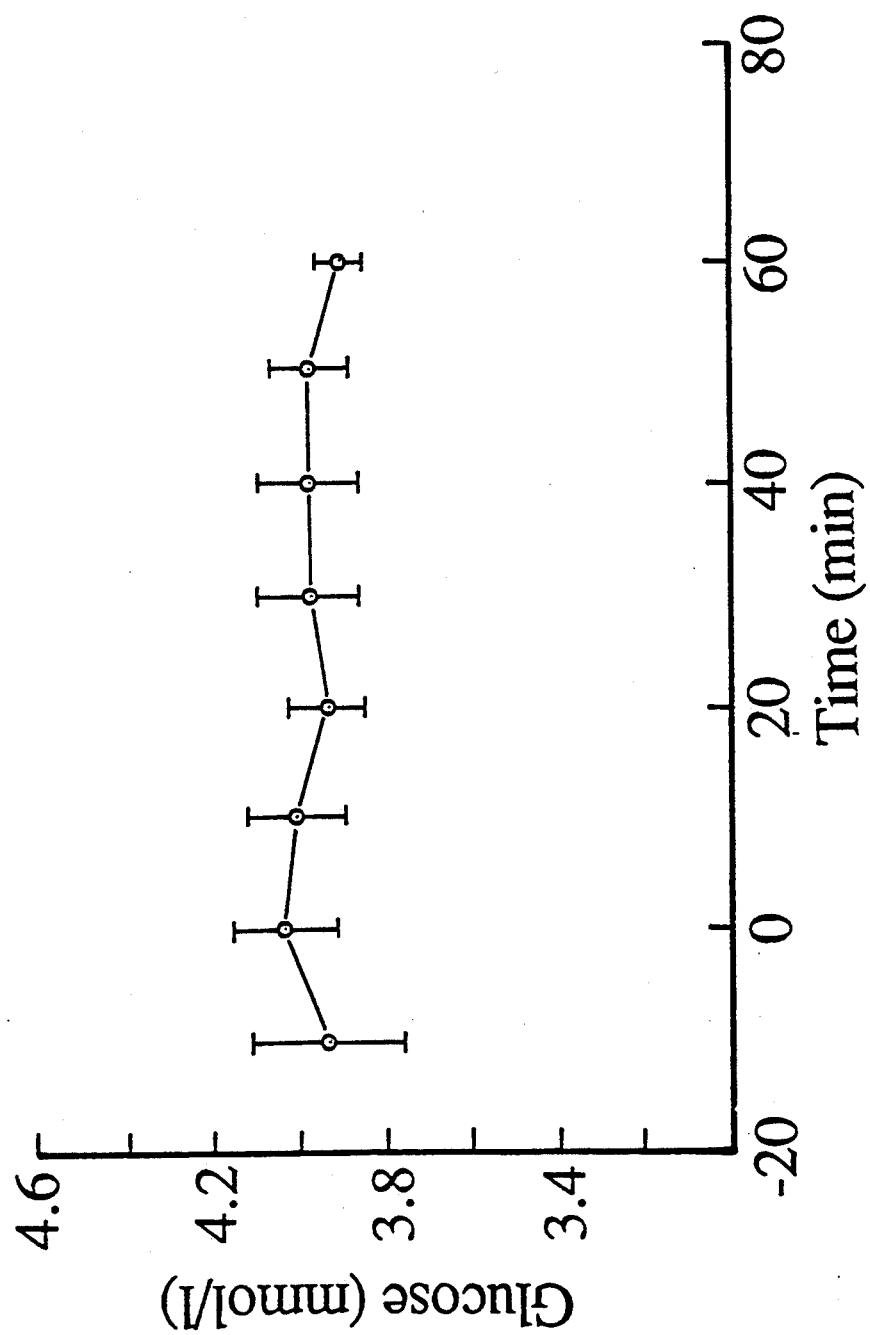
FIG. 6 shows plasma glucose levels in man obtained for administration intranasally of starch microspheres (control)
Figure 7:
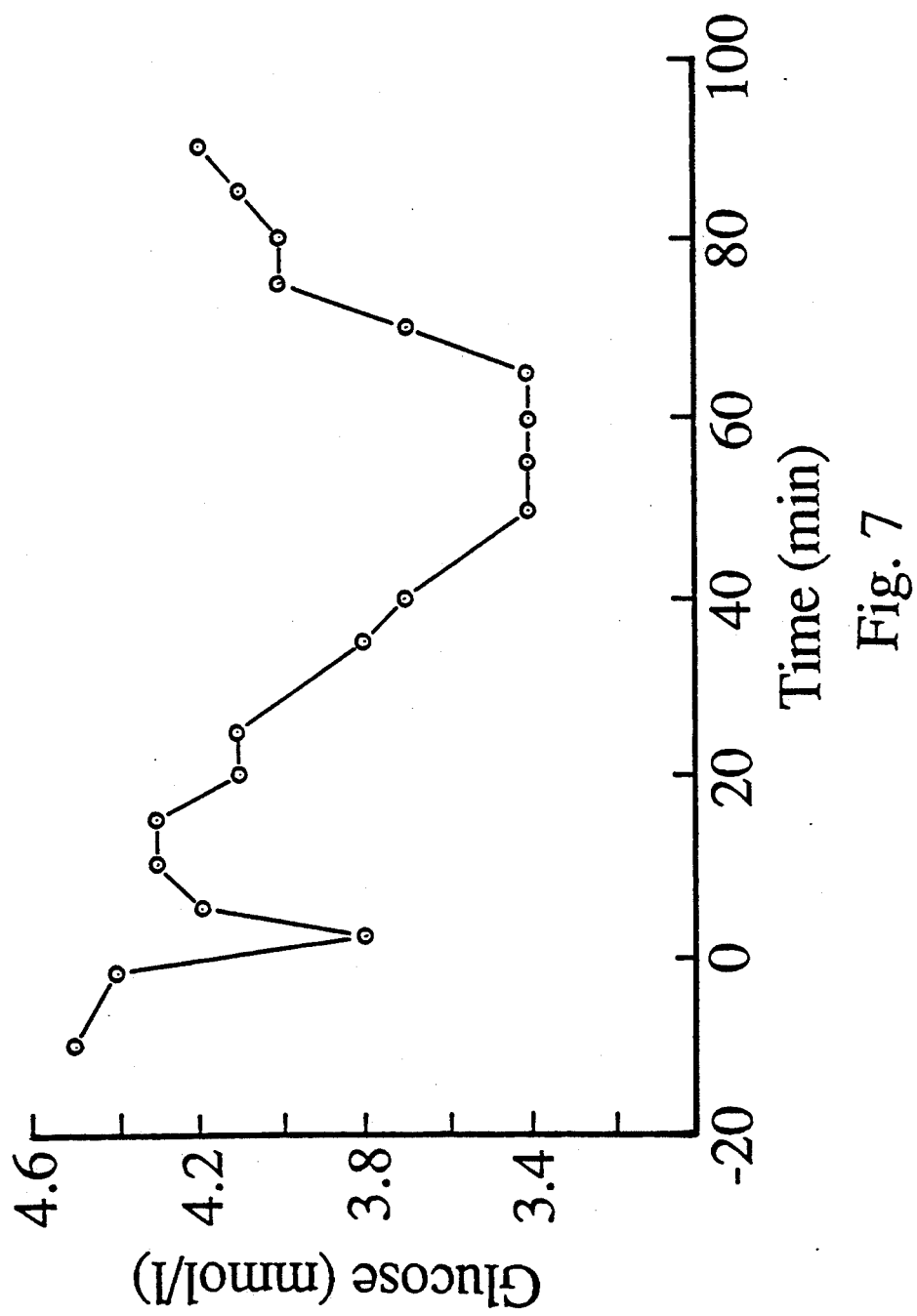
FIG. 7 shows plasma glucose levels in one selected subject obtained for administration intranasally of insulin in combination with starch microspheres.

FIGS. 5 and 6 (n=5) show that the plasma glucose levels obtained when administering microspheres alone do not show any decrease whereas a significant decrease in plasma glucose level is obtained when administering the insulin in combination with the microspheres. FIG. 7 shows data from subject D with a plasma glucose level decreasing from 4.5 to 3.4 mmol/l after administration of 1 IU/kg insulin in combination with the starch microspheres.

EXAMPLE 3: Stability studies

It has been shown that peptides and proteins such as insulin are susceptible to degradation by mucosal enzymes such as aminopeptidases. Experiments were carried out to study whether a peptide or a protein encapsulated in a microsphere system would to a certain degree be protected against such an enzymatic degradation normally taking place in the nasal cavity.

Insulin in 0.1 M Tris buffer (5.6 IU/ml) or incorporated into albumin microspheres (0.4 IU/ml) were incubated with 1.0 ml of a 0.05% trypsin solution for up to 180 min. Samples were withdrawn at suitable time intervals and assayed for content of non-degraded insulin.

Figure 8:
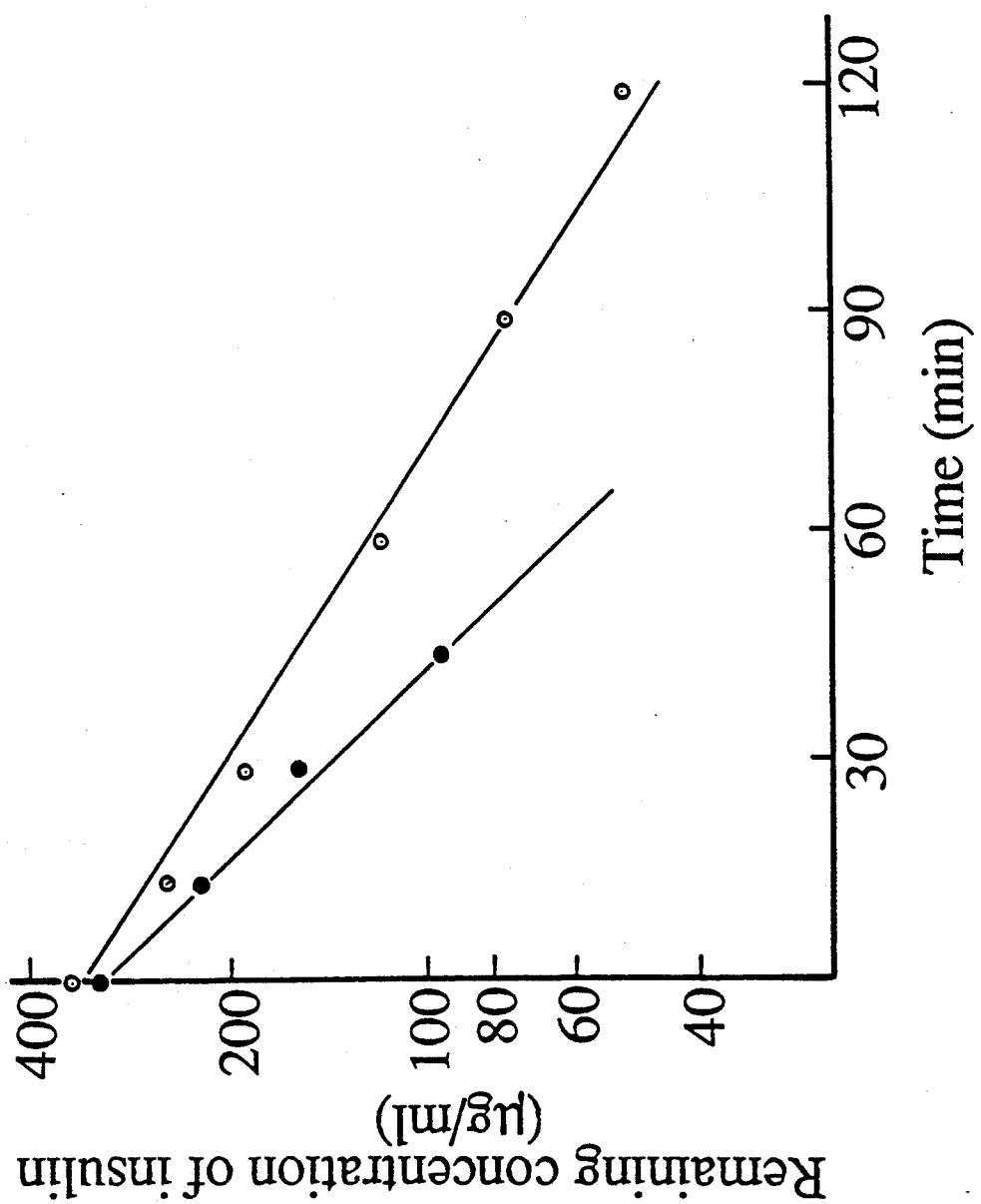
FIG. 8 shows the protection of insulin incorporated into microspheres against enzymatic degradation.

FIG. 8 shows how the microsphere system of the present invention, which in this example comprises albumin, can protect a drug, in this example insulin, against enzymatic degradation. This will be of importance in protecting peptides and proteins against degradation in the nasal mucosa after application.

Legend to Figures

FIG. 1

○ Starch microspheres
● Insulin solution
△ Insulin+starch microspheres
Insulin administered I.V.

FIG. 2

○ Starch microspheres
● Starch solution
△ Insulin+starch microspheres

I claim:

1. A drug delivery composition which is suitable for transmucosal delivery and which comprises a plurality of microspheres adapted to gel in contact with the mucosal surface and active drug associated with each microsphere, the composition being substantially free of an enhancer, characterised in that the drug is for systemic delivery and is a peptide having a maximum molecular weight of 6000, and the microspheres comprise starch, gelatin, collagen or dextran.

2. A drug delivery composition as claimed in claim 1 in which the microspheres are starch microspheres of an average diameter of between 10 and 100 μm.

3. A drug delivery composition as claimed in claim 1 wherein the microsphere material is at least partially cross-linked.

4. A drug delivery composition as claimed in claim 1 wherein the microspheres are formed from the active drug itself.

5. A drug delivery composition as claimed in claim 1 wherein the microspheres are suitable for administration to the vagina.

6. A drug delivery composition as claimed in claim 1 wherein the microspheres are suitable for administration to the eye.

7. A drug delivery composition as claimed in claim 1 wherein the microspheres are suitable for delivery to the nasal mucosa.

8. A drug delivery composition as claimed in claim 1 and which is a vaccine.

9. A drug delivery composition according to claim 1 wherein the peptide has a molecular weight of at least 1000.

10. A drug delivery composition as claimed in claim 1 wherein the peptide is insulin or a calcitonin.

11. A drug delivery composition as claimed in claim 1 wherein the drug is associated with the microspheres by being incorporated therein.

12. A drug delivery composition as claimed in claim 11 wherein the drug is incorporated into the microspheres during preparation of the microspheres.

13. A drug delivery composition as claimed in claim 11 wherein the drug is incorporated into the microspheres after preparation of the microspheres.

* * * * *

UNITED STATES PATENT AND TRADEMARK OFFICE
CERTIFICATE OF CORRECTION

PATENT NO. : 5,204,108
DATED : April 20, 1993
INVENTOR(S) : Lisbeth Illum

It is certified that error appears in the above-indentified patent and that said Letters Patent is hereby corrected as shown below:

Col. 2, line 2, after "being" insert --suggested are those that are poorly absorbed orally or--;

Col. 2, line 3, after "either" delete ".in" and insert --in--;

Col 2, line 63, after "system" insert --after preparation. The effectiveness of the system can be--; and Col. 8, line 10, before "Insulin" insert --▲--.

Signed and Sealed this

First Day of March, 1994

Attest:

BRUCE LEHMAN

*Attesting Officer*  *Commissioner of Patents and Trademarks*